US011666246B2

(12) United States Patent
Kusens

(10) Patent No.: US 11,666,246 B2
(45) Date of Patent: Jun. 6, 2023

(54) METHODS AND SYSTEMS FOR ASSIGNING LOCATIONS TO DEVICES

(71) Applicant: CERNER INNOVATION, INC., Kansas City, KS (US)

(72) Inventor: Michael Kusens, Cooper City, FL (US)

(73) Assignee: Cerner Innovation, Inc., Kansas City, KS (US)

( * ) Notice: Subject to any disclaimer, the term of this patent is extended or adjusted under 35 U.S.C. 154(b) by 0 days.

(21) Appl. No.: 17/101,639

(22) Filed: Nov. 23, 2020

(65) Prior Publication Data

US 2021/0068709 A1  Mar. 11, 2021

Related U.S. Application Data

(63) Continuation of application No. 15/395,243, filed on Dec. 30, 2016, now Pat. No. 10,878,220.
(Continued)

(51) Int. Cl.
*G16H 30/20* (2018.01)
*H04N 7/18* (2006.01)
(Continued)

(52) U.S. Cl.
CPC .............. *A61B 5/11* (2013.01); *A61B 5/0077* (2013.01); *A61B 5/1176* (2013.01);
(Continued)

(58) Field of Classification Search
CPC ....... A61B 5/11; A61B 5/0077; A61B 5/4064; A61B 5/746; A61B 5/1176; G16H 40/20; G16H 20/10; G16H 30/20; G16H 15/00; G16H 80/00; G16H 40/67; G16H 50/30; G16H 40/63; G16H 10/60; G16H 5/23293; G16H 7/183; H04N 13/204; H04N 13/207;
(Continued)

(56) References Cited

U.S. PATENT DOCUMENTS 4,669,263 A  6/1987 Sugiyama
4,857,716 A  8/1989 Gombrich et al.
(Continued)

FOREIGN PATENT DOCUMENTS

DE    19844918 A1    4/2000
WO   2007/081629 A2   7/2007
(Continued)

OTHER PUBLICATIONS

Notice of Allowance received for U.S. Appl. No. 16/654,502, dated Feb. 17, 2021, 9 pages.
(Continued)

*Primary Examiner* — Alazar Tilahun
(74) *Attorney, Agent, or Firm* — Kilpatrick Townsend & Stockton LLP

(57) ABSTRACT

A location identification system analyzes information received corresponding to a device detected in a room of a patient. On detecting a location identification of the device, the system assigns the device to the location corresponding to the location identification. In embodiments, the system retrieves patient and care team information for the location. The location and patient and care team information may be communicated to a central video monitoring system.

20 Claims, 6 Drawing Sheets

Related U.S. Application Data

(60) Provisional application No. 62/273,735, filed on Dec. 31, 2015.

(51) Int. Cl.

| | | |
|---|---|---|
| *H04N 13/204* | (2018.01) | |
| *G16H 15/00* | (2018.01) | |
| *G16H 40/63* | (2018.01) | |
| *H04N 13/207* | (2018.01) | |
| *A61B 5/11* | (2006.01) | |
| *G08B 5/22* | (2006.01) | |
| *G08B 25/00* | (2006.01) | |
| *G08B 21/18* | (2006.01) | |
| *G06T 7/292* | (2017.01) | |
| *G06T 7/20* | (2017.01) | |
| *G16H 10/60* | (2018.01) | |
| *G16H 40/20* | (2018.01) | |
| *G06V 20/52* | (2022.01) | |
| *G06V 20/64* | (2022.01) | |
| *G06V 40/20* | (2022.01) | |
| *G06V 40/16* | (2022.01) | |
| *G06F 18/22* | (2023.01) | |
| *H04N 23/63* | (2023.01) | |
| *A61B 5/00* | (2006.01) | |
| *G06T 7/00* | (2017.01) | |
| *G06T 11/60* | (2006.01) | |
| *A61B 5/1171* | (2016.01) | |
| *G08B 13/196* | (2006.01) | |
| *G16H 80/00* | (2018.01) | |
| *G16H 40/67* | (2018.01) | |
| *G16H 50/30* | (2018.01) | |
| *G16H 20/10* | (2018.01) | |
| *G08B 21/04* | (2006.01) | |
| *H04N 13/00* | (2018.01) | |
| *G06F 3/0482* | (2013.01) | |
| *G06F 3/04847* | (2022.01) | |

(52) U.S. Cl.
CPC .......... *A61B 5/4064* (2013.01); *A61B 5/746* (2013.01); *G06F 18/22* (2023.01); *G06T 7/0012* (2013.01); *G06T 7/0016* (2013.01); *G06T 7/20* (2013.01); *G06T 7/292* (2017.01); *G06T 11/60* (2013.01); *G06V 20/52* (2022.01); *G06V 20/647* (2022.01); *G06V 40/172* (2022.01); *G06V 40/20* (2022.01); *G08B 5/22* (2013.01); *G08B 13/196* (2013.01); *G08B 21/182* (2013.01); *G08B 25/009* (2013.01); *G16H 10/60* (2018.01); *G16H 15/00* (2018.01); *G16H 20/10* (2018.01); *G16H 30/20* (2018.01); *G16H 40/20* (2018.01); *G16H 40/63* (2018.01); *G16H 40/67* (2018.01); *G16H 50/30* (2018.01); *G16H 80/00* (2018.01); *H04N 7/18* (2013.01); *H04N 7/181* (2013.01); *H04N 7/183* (2013.01); *H04N 13/204* (2018.05); *H04N 13/207* (2018.05); *H04N 23/63* (2023.01); *G06F 3/0482* (2013.01); *G06F 3/04847* (2013.01); *G06T 2200/04* (2013.01); *G06T 2200/24* (2013.01); *G06T 2207/10012* (2013.01); *G06T 2207/10021* (2013.01); *G06T 2207/10024* (2013.01); *G06T 2207/20221* (2013.01); *G06T 2207/30201* (2013.01); *G06T 2207/30232* (2013.01); *G06V 40/161* (2022.01); *G08B 13/19639* (2013.01); *G08B 21/0476* (2013.01); *H04N 2013/0085* (2013.01)

(58) Field of Classification Search
CPC ...... H04N 7/18; H04N 5/23293; H04N 7/183; H04N 7/181; H04N 2013/0085; G06K 9/00771; G06K 9/6215; G06K 9/00288; G06K 9/00335; G06K 9/52; G06K 9/00208; G06K 9/4604; G06K 9/00228; G06T 7/0016; G06T 11/60; G06T 7/0012; G06T 7/292; G06T 7/20; G06T 2200/24; G06T 2207/10012; G06T 2007/20221; G06T 2207/30201; G06T 2207/10021; G06T 2207/10024; G06T 2207/30232; G06T 2200/04; G08B 13/196; G08B 5/22; G08B 25/009; G08B 21/182; G08B 13/19639; G08B 21/0476

See application file for complete search history.

(56) References Cited

U.S. PATENT DOCUMENTS

| | | |
|---|---|---|
| 5,031,228 A | 7/1991 | Lu |
| 5,276,432 A | 1/1994 | Travis |
| 5,448,221 A | 9/1995 | Weller |
| 5,482,050 A | 1/1996 | Smokoff et al. |
| 5,592,153 A | 1/1997 | Welling et al. |
| 5,798,798 A | 8/1998 | Rector et al. |
| 5,838,223 A | 11/1998 | Gallant et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,160,478 A | 12/2000 | Jacobsen et al. |
| 6,174,283 B1 | 1/2001 | Nevo et al. |
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,614,349 B1 | 9/2003 | Proctor et al. |
| 6,727,818 B1 | 4/2004 | Wildman et al. |
| 6,804,656 B1 | 10/2004 | Rosenfeld et al. |
| 7,015,816 B2 | 3/2006 | Wildman et al. |
| 7,122,005 B2 | 10/2006 | Shusterman |
| 7,154,397 B2 | 12/2006 | Zerhusen et al. |
| 7,237,287 B2 | 7/2007 | Weismiller et al. |
| 7,323,991 B1 | 1/2008 | Eckert et al. |
| 7,408,470 B2 | 8/2008 | Wildman et al. |
| 7,420,472 B2 | 9/2008 | Tran |
| 7,430,608 B2 | 9/2008 | Noonan et al. |
| 7,502,498 B2 | 3/2009 | Wen et al. |
| 7,612,679 B1 | 11/2009 | Fackler et al. |
| 7,669,263 B2 | 3/2010 | Menkedick et al. |
| 7,715,387 B2 | 5/2010 | Schuman |
| 7,724,147 B2 | 5/2010 | Brown |
| 7,756,723 B2 | 7/2010 | Rosow et al. |
| 7,890,349 B2 | 2/2011 | Cole et al. |
| 7,893,842 B2 | 2/2011 | Deutsch |
| 7,895,055 B2 | 2/2011 | Schneider et al. |
| 7,908,153 B2 | 3/2011 | Scherpbier et al. |
| 7,945,457 B2 | 5/2011 | Zaleski |
| 7,962,544 B2 | 6/2011 | Torok et al. |
| 7,972,140 B2 | 7/2011 | Renaud |
| 8,108,036 B2 | 1/2012 | Tran |
| 8,123,685 B2 | 2/2012 | Brauers et al. |
| 8,128,596 B2 | 3/2012 | Carter |
| 8,190,447 B2 | 5/2012 | Hungerford et al. |
| 8,224,108 B2 | 7/2012 | Steinberg et al. |
| 8,237,558 B2 | 8/2012 | Seyed et al. |
| 8,273,018 B1 | 9/2012 | Fackler et al. |
| 8,432,263 B2 | 4/2013 | Kunz |
| 8,451,314 B1 | 5/2013 | Cline et al. |
| 8,529,448 B2 | 9/2013 | Mcnair |
| 8,565,500 B2 | 10/2013 | Neff |
| 8,620,682 B2 | 12/2013 | Bechtel et al. |
| 8,655,680 B2 | 2/2014 | Bechtel et al. |

(56) References Cited

U.S. PATENT DOCUMENTS

| | | |
|---|---|---|
| 8,700,423 B2 | 4/2014 | Eaton et al. |
| 8,727,981 B2 | 5/2014 | Bechtel et al. |
| 8,769,153 B2 | 7/2014 | Dziubinski |
| 8,890,937 B2 | 11/2014 | Skubic et al. |
| 8,902,068 B2 | 12/2014 | Bechtel et al. |
| 8,917,186 B1 | 12/2014 | Grant |
| 8,953,886 B2 | 2/2015 | King et al. |
| 9,072,929 B1 | 7/2015 | Rush et al. |
| 9,129,506 B1 | 9/2015 | Kusens |
| 9,147,334 B2 | 9/2015 | Long et al. |
| 9,159,215 B1 | 10/2015 | Kusens |
| 9,269,012 B2 | 2/2016 | Fotland |
| 9,292,089 B1 | 3/2016 | Sadek |
| 9,305,191 B2 | 4/2016 | Long et al. |
| 9,408,561 B2 | 8/2016 | Stone et al. |
| 9,424,699 B2 | 8/2016 | Kusens et al. |
| 9,466,163 B2 | 10/2016 | Kusens et al. |
| 9,489,820 B1 | 11/2016 | Kusens |
| 9,519,969 B1 | 12/2016 | Kusens |
| 9,524,443 B1 | 12/2016 | Kusens |
| 9,536,310 B1 | 1/2017 | Kusens |
| 9,538,158 B1 | 1/2017 | Rush et al. |
| 9,563,955 B1 | 2/2017 | Kamarshi et al. |
| 9,597,016 B2 | 3/2017 | Stone et al. |
| 9,691,206 B2 | 6/2017 | Kusens et al. |
| 9,729,833 B1 | 8/2017 | Kusens |
| 9,741,227 B1 | 8/2017 | Kusens |
| 9,774,991 B2 | 9/2017 | Kusens |
| 9,838,849 B2 | 12/2017 | Kusens |
| 9,858,741 B2 | 1/2018 | Kusens et al. |
| 9,892,310 B2 | 2/2018 | Kusens et al. |
| 9,892,311 B2 | 2/2018 | Kusens et al. |
| 9,892,611 B1 | 2/2018 | Kusens |
| 9,905,113 B2 | 2/2018 | Kusens |
| 9,934,427 B2 | 4/2018 | Derenne et al. |
| 9,984,521 B1 | 5/2018 | Kusens et al. |
| 9,997,001 B2 | 6/2018 | Kusens et al. |
| 9,998,857 B2 | 6/2018 | Kusens |
| 10,013,831 B1 | 7/2018 | Kusens et al. |
| 10,068,116 B2 * | 9/2018 | Good .................. G01S 5/0289 |
| 10,078,956 B1 | 9/2018 | Kusens |
| 10,090,068 B2 | 10/2018 | Kusens et al. |
| 10,091,463 B1 | 10/2018 | Kusens |
| 10,096,223 B1 | 10/2018 | Kusens |
| 10,109,179 B2 | 10/2018 | Kusens |
| 10,115,253 B2 | 10/2018 | Kusens et al. |
| 10,115,254 B1 | 10/2018 | Kusens et al. |
| 10,121,299 B2 | 11/2018 | Kusens et al. |
| 10,210,378 B2 | 2/2019 | Kusens et al. |
| 10,225,522 B1 | 3/2019 | Kusens |
| 10,342,478 B2 | 7/2019 | Kusens |
| 10,524,722 B2 | 1/2020 | Kusens et al. |
| 10,643,061 B2 | 5/2020 | Kusens et al. |
| 10,922,936 B2 | 2/2021 | Kusens et al. |
| 10,922,946 B2 | 2/2021 | Kusens et al. |
| 2002/0015034 A1 | 2/2002 | Malmborg |
| 2002/0038073 A1 | 3/2002 | August |
| 2002/0077863 A1 | 6/2002 | Rutledge et al. |
| 2002/0101349 A1 | 8/2002 | Rojas |
| 2002/0115905 A1 | 8/2002 | August |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0135390 A1 | 7/2003 | Obrien et al. |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0052418 A1 | 3/2004 | Delean |
| 2004/0054760 A1 | 3/2004 | Ewing et al. |
| 2004/0097227 A1 | 5/2004 | Siegel |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0182305 A1 | 8/2005 | Hendrich |
| 2005/0231341 A1 | 10/2005 | Shimizu |
| 2005/0249139 A1 | 11/2005 | Nesbit |
| 2006/0004606 A1 | 1/2006 | Wendl et al. |
| 2006/0047538 A1 | 3/2006 | Condurso et al. |
| 2006/0049936 A1 | 3/2006 | Collins et al. |
| 2006/0058587 A1 | 3/2006 | Heimbrock et al. |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0145874 A1 | 7/2006 | Fredriksson et al. |
| 2006/0261974 A1 | 11/2006 | Albert et al. |
| 2007/0033072 A1 | 2/2007 | Bildirici |
| 2007/0083445 A1 | 4/2007 | Garcia et al. |
| 2007/0085690 A1 | 4/2007 | Tran |
| 2007/0118054 A1 | 5/2007 | Pinhas et al. |
| 2007/0120689 A1 | 5/2007 | Zerhusen et al. |
| 2007/0129983 A1 | 6/2007 | Scherpbier et al. |
| 2007/0136102 A1 | 6/2007 | Rodgers |
| 2007/0136218 A1 | 6/2007 | Bauer et al. |
| 2007/0159332 A1 | 7/2007 | Koblasz |
| 2007/0279219 A1 | 12/2007 | Warriner |
| 2007/0296600 A1 | 12/2007 | Dixon et al. |
| 2008/0001735 A1 | 1/2008 | Tran |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0021731 A1 * | 1/2008 | Rodgers .................. A61B 5/1113 <br> 705/2 |
| 2008/0071210 A1 | 3/2008 | Moubayed et al. |
| 2008/0087719 A1 | 4/2008 | Sahud |
| 2008/0106374 A1 | 5/2008 | Sharbaugh |
| 2008/0126132 A1 | 5/2008 | Warner et al. |
| 2008/0228045 A1 | 9/2008 | Gao et al. |
| 2008/0249376 A1 | 10/2008 | Zaleski |
| 2008/0267447 A1 | 10/2008 | Kelusky et al. |
| 2008/0277486 A1 | 11/2008 | Seem et al. |
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1 | 4/2009 | Salgo et al. |
| 2009/0112630 A1 | 4/2009 | Collins et al. |
| 2009/0119843 A1 | 5/2009 | Rodgers et al. |
| 2009/0177327 A1 | 7/2009 | Turner et al. |
| 2009/0224924 A1 | 9/2009 | Thorp |
| 2009/0278934 A1 | 11/2009 | Ecker et al. |
| 2009/0322513 A1 | 12/2009 | Hwang et al. |
| 2009/0326340 A1 | 12/2009 | Wang et al. |
| 2010/0117836 A1 | 5/2010 | Seyed et al. |
| 2010/0169114 A1 | 7/2010 | Henderson et al. |
| 2010/0169120 A1 | 7/2010 | Herbst et al. |
| 2010/0172567 A1 | 7/2010 | Prokoski |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |
| 2011/0018709 A1 | 1/2011 | Kombluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |
| 2011/0035466 A1 | 2/2011 | Panigrahi |
| 2011/0050411 A1 * | 3/2011 | Schuman ............... G08B 21/22 <br> 340/539.13 |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1 | 4/2011 | Aarts |
| 2011/0087125 A1 | 4/2011 | Causevic |
| 2011/0102133 A1 | 5/2011 | Shaffer |
| 2011/0102181 A1 | 5/2011 | Metz et al. |
| 2011/0106560 A1 | 5/2011 | Eaton et al. |
| 2011/0106561 A1 | 5/2011 | Eaton et al. |
| 2011/0175809 A1 | 7/2011 | Markovic et al. |
| 2011/0190593 A1 | 8/2011 | Mcnair |

(56) References Cited

U.S. PATENT DOCUMENTS

| | | |
|---|---|---|
| 2011/0227740 A1 | 9/2011 | Wohltjen |
| 2011/0245707 A1 | 10/2011 | Castle et al. |
| 2011/0254682 A1 | 10/2011 | Sigrist |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0016295 A1 | 1/2012 | Tsoukalis |
| 2012/0025991 A1 | 2/2012 | Okeefe et al. |
| 2012/0026308 A1 | 2/2012 | Johnson et al. |
| 2012/0075464 A1 | 3/2012 | Derenne et al. |
| 2012/0092162 A1 | 4/2012 | Rosenberg |
| 2012/0098918 A1 | 4/2012 | Murphy |
| 2012/0140068 A1* | 6/2012 | Monroe ............ H04N 7/183 348/143 |
| 2012/0154582 A1* | 6/2012 | Johnson ............ G16H 10/60 348/143 |
| 2012/0212582 A1 | 8/2012 | Deutsch |
| 2012/0259650 A1 | 10/2012 | Mallon et al. |
| 2012/0314901 A1 | 12/2012 | Hanson et al. |
| 2012/0323090 A1 | 12/2012 | Bechtel et al. |
| 2012/0323591 A1 | 12/2012 | Bechtel et al. |
| 2012/0323592 A1 | 12/2012 | Bechtel et al. |
| 2013/0027199 A1 | 1/2013 | Bonner |
| 2013/0028570 A1 | 1/2013 | Suematsu et al. |
| 2013/0120120 A1 | 5/2013 | Long et al. |
| 2013/0122807 A1 | 5/2013 | Fenarvitz et al. |
| 2013/0127620 A1 | 5/2013 | Siebers et al. |
| 2013/0184592 A1 | 7/2013 | Venetianer et al. |
| 2013/0265482 A1 | 10/2013 | Funamoto |
| 2013/0309128 A1 | 11/2013 | Voegeli et al. |
| 2013/0332184 A1 | 12/2013 | Burnham et al. |
| 2014/0039351 A1 | 2/2014 | Mix et al. |
| 2014/0070950 A1 | 3/2014 | Snodgrass |
| 2014/0081654 A1 | 3/2014 | Bechtel et al. |
| 2014/0085501 A1 | 3/2014 | Tran |
| 2014/0086450 A1 | 3/2014 | Huang et al. |
| 2014/0108041 A1 | 4/2014 | Bechtel et al. |
| 2014/0155755 A1 | 6/2014 | Pinter et al. |
| 2014/0168397 A1* | 6/2014 | Greco ............ G08B 21/0227 348/77 |
| 2014/0191861 A1 | 7/2014 | Scherrer |
| 2014/0191946 A1 | 7/2014 | Cho et al. |
| 2014/0213845 A1 | 7/2014 | Bechtel et al. |
| 2014/0267625 A1 | 9/2014 | Clark et al. |
| 2014/0267736 A1 | 9/2014 | Delean |
| 2014/0309789 A1 | 10/2014 | Ricci |
| 2014/0327545 A1 | 11/2014 | Bolling et al. |
| 2014/0328512 A1 | 11/2014 | Gurwicz et al. |
| 2014/0333744 A1 | 11/2014 | Baym et al. |
| 2014/0333776 A1 | 11/2014 | Dedeoglu et al. |
| 2014/0354436 A1 | 12/2014 | Nix et al. |
| 2014/0365242 A1 | 12/2014 | Neff |
| 2015/0057635 A1 | 2/2015 | Bechtel et al. |
| 2015/0061891 A1 | 3/2015 | Oleson et al. |
| 2015/0109442 A1* | 4/2015 | Derenne ............ H04N 7/185 348/143 |
| 2015/0206415 A1 | 7/2015 | Wegelin et al. |
| 2015/0269318 A1 | 9/2015 | Neff |
| 2015/0278456 A1 | 10/2015 | Bermudez Rodriguez et al. |
| 2015/0294143 A1 | 10/2015 | Wells et al. |
| 2016/0022218 A1 | 1/2016 | Hayes et al. |
| 2016/0029160 A1* | 1/2016 | Theurer ............ G16Z 99/00 455/456.1 |
| 2016/0070869 A1 | 3/2016 | Portnoy |
| 2016/0093195 A1 | 3/2016 | Ophardt |
| 2016/0098676 A1 | 4/2016 | Kusens et al. |
| 2016/0127641 A1 | 5/2016 | Gove |
| 2016/0180668 A1 | 6/2016 | Kusens et al. |
| 2016/0183864 A1 | 6/2016 | Kusens et al. |
| 2016/0217347 A1 | 7/2016 | Mineo |
| 2016/0253802 A1 | 9/2016 | Venetianer et al. |
| 2016/0267327 A1 | 9/2016 | Franz et al. |
| 2016/0285416 A1* | 9/2016 | Tiwari ............ H02S 50/15 |
| 2016/0314258 A1 | 10/2016 | Kusens |
| 2016/0324460 A1 | 11/2016 | Kusens |
| 2016/0360970 A1 | 12/2016 | Tzvieli et al. |
| 2017/0055917 A1 | 3/2017 | Stone et al. |
| 2017/0084158 A1 | 3/2017 | Kusens |
| 2017/0091562 A1 | 3/2017 | Kusens |
| 2017/0109991 A1 | 4/2017 | Kusens |
| 2017/0116473 A1 | 4/2017 | Sashida et al. |
| 2017/0143240 A1 | 5/2017 | Stone et al. |
| 2017/0163949 A1 | 6/2017 | Suzuki |
| 2017/0193177 A1 | 7/2017 | Kusens |
| 2017/0214902 A1 | 7/2017 | Braune |
| 2017/0289503 A1 | 10/2017 | Kusens |
| 2017/0337682 A1 | 11/2017 | Liao et al. |
| 2018/0018864 A1 | 1/2018 | Baker |
| 2018/0068545 A1 | 3/2018 | Kusens |
| 2018/0104409 A1 | 4/2018 | Bechtel et al. |
| 2018/0144605 A1 | 5/2018 | Kusens |
| 2018/0189946 A1 | 7/2018 | Kusens et al. |
| 2018/0190098 A1 | 7/2018 | Kusens |
| 2018/0357875 A1 | 12/2018 | Kusens |
| 2019/0006046 A1 | 1/2019 | Kusens et al. |
| 2019/0029528 A1 | 1/2019 | Tzvieli et al. |
| 2019/0043192 A1 | 2/2019 | Kusens et al. |
| 2019/0057592 A1 | 2/2019 | Kusens |
| 2019/0205630 A1 | 7/2019 | Kusens |
| 2019/0206218 A1 | 7/2019 | Kusens et al. |
| 2019/0209022 A1 | 7/2019 | Sobol et al. |
| 2019/0228866 A1 | 7/2019 | Weffers-Albu et al. |
| 2019/0261915 A1 | 8/2019 | Kusens |
| 2019/0307405 A1 | 10/2019 | Terry et al. |
| 2019/0318478 A1 | 10/2019 | Kusens et al. |
| 2020/0050844 A1 | 2/2020 | Kusens |
| 2021/0202052 A1 | 7/2021 | Bechtel et al. |

FOREIGN PATENT DOCUMENTS

| | | |
|---|---|---|
| WO | 2009/018422 A1 | 2/2009 |
| WO | 2012/122002 A1 | 9/2012 |
| WO | 2016/126845 A1 | 8/2016 |
| WO | 2017/058991 A1 | 4/2017 |
| WO | 2017/124056 A1 | 7/2017 |
| WO | 2018/218286 A1 | 12/2018 |

OTHER PUBLICATIONS

Non-Final Office action received for U.S. Appl. No. 16/410,745, dated May 21, 2021, 21 pages.

Conaire et al., "Fusion of Infrared and Visible Spectrum Video for Indoor Surveillance", WIAMIS, Apr. 2005, 4 pages.

Mooney, Tom, "Rhode Island ER First to Test Google Glass on Medical Conditions", EMS1, Available online at: <https://www.ems1.com/ems-products/technology/articles/1860487-Rhode-Island-ER-first-to-test-Google-Glass-on-medical-conditions/>, Mar. 10, 2014, 3 pages.

Raheja et al., "Human Facial Expression Detection From Detected in Captured Image Using Back Propagation Neural Network", International Journal of Computer Science and Information Technology (IJCSIT), vol. 2, No. 1, Feb. 2010, 9 pages.

"Virtual Patient Observation: Centralize Monitoring of High-Risk Patients with Video", CISCO, Cisco Video Surveillance Manager, 2013, pp. 1-6.

Notice of Allowance received for U.S. Appl. No. 16/410,745, dated Jan. 4, 2022, 10 pages.

Non-Final Office Action received for U.S. Appl. No. 16/830,498, dated Sep. 22, 2021, 29 pages.

Notice of Allowance received for U.S. Appl. No. 16/816,626, dated Sep. 30, 2021, 9 pages.

Quan et al., "Facial Asymmetry Analysis Based on 3-D Dynamic Scans", 2012 IEEE International Conference on Systems, Man, and Cybernetics; COEX, Seoul, Korea; DOI: 10.1109/ICSMC.2012.6378151, Oct. 14-17, 2012, pp. 2676-2681.

Non-Final Office action received for U.S. Appl. No. 17/117,414, dated Jul. 27, 2021, 12 pages.

Pre-interview First Office Action received for U.S. Appl. No. 16/731,274, dated Sep. 1, 2021, 12 pages.

(56) References Cited

OTHER PUBLICATIONS

Non-Final Office Action received for U.S. Appl. No. 17/152,403, dated Mar. 15, 2022, 10 pages.
Notice of Allowance received for U.S. Appl. No. 17/318,521, dated Aug. 31, 2022, 9 pages.
Otanasap et al., "Pre-Impact Fall Detection System Using Dynamic Threshold and 3D Bounding Box", SPIE.Digital Library, Proceedings vol. 10225, Eighth International Conference on Graphic and Image Processing (ICGIP 2016), Available online at: <https://doi.org/10.1117/12.2266822>, Feb. 8, 2017, pp. 1-6.
Zarka et al., "Real-Time Human Motion Detection and Tracking", IEEE, Available online at: <https://ieeexplore.IEEE.org/document/4530098>, 2008, pp. 1-6.

* cited by examiner

Patient Onboarding

Cardiology 101-A

- Patient Name: John Henderson
- Language: English
- Hearing Impared: Yes
- RN Name: Nancy Johnson
- RN Ext: 7856
- Room:
  - DeviceWorks Hospital
    - DeviceWorks Hospital
      - 12North
        - 1209
          - A Save   Clear All   Cancel

FIG. 7

File  Edit  View  Options  Help

Add   Access Media   Grid Views   Commands   Web Settings   Plugins   Settings

PT: Matt RM: 1231 RN: Bonny EXT: 8891

FIG. 8

METHODS AND SYSTEMS FOR ASSIGNING LOCATIONS TO DEVICES

CROSS-REFERENCE TO RELATED APPLICATIONS

This application is a continuation of U.S. patent application Ser. No. 15/395,243, entitled "Methods and Systems for Assigning Locations to Devices," filed Dec. 30, 2016, which claims the benefit of U.S. Provisional Application Ser. No. 62/273,735, entitled "Methods and Systems for Detecting Stroke Symptoms," filed Dec. 31, 2015, herein incorporated by reference in its entirety, and is related to commonly assigned U.S. patent application Ser. No. 15/395,250, entitled "Methods and Systems for Detecting Prohibited Objects in a Patient Room," filed Dec. 30, 2016, and U.S. patent application Ser. No. 15/395,526, entitled "Detecting Unauthorized Visitors," filed Dec. 30, 2016.

BACKGROUND

Medical facilities, such as hospitals, face many challenges in addition to simply caring for patients. For example, securing patients and equipment (e.g., medical devices) consumes many resources and current methods lack effectiveness. In addition to requiring personnel to physically monitor locations within the facility, visitor logs and visitor badges, and radio-frequency identification (RFID) technology are often utilized to control access to certain locations within the facility. However, each of these require subjective decision-making and are prone to error by the personnel monitoring the locations or assisting visitors signing a visitor log and issuing visitor badges accordingly. Further, none of these methods necessarily prevent an authorized visitor from breaching areas of the facility where the authorized visitor is not authorized. For example, a visitor may be authorized to visit a particular patient but, based on some condition of the patient, may not have close contact with the patient. In contrast, a caregiver of the same patient may need to have close contact with the patient. Additionally, in some situations, an authorized visitor may unwittingly provide contraband (e.g., some thing or some object a particular patient is not allowed) to a patient that the current methods are unable to detect. Finally, medical devices are constantly being shuffled between patients and locations within a facility. Tracking the locations of these devices can be extremely difficult. Accordingly, overall security for patients and equipment suffers and the many resources currently being utilized are wasted.

BRIEF SUMMARY

This brief summary is provided as a general overview of the more detailed disclosure which follows. It is not intended to identify key or essential elements of the disclosure, or to define the claim terms in isolation from the remainder of the disclosure, including the drawings.

This disclosure generally relates to systems and method for assigning locations to devices. Generally, and without limitation, the method involves identifying a signal from a location beacon corresponding to a location of the device, a location identification visible on a visual location identifier tag of the location, or a location identification selected by a user. Accordingly, the system assigns the location corresponding to the signal or the location identification to the device. The system may also retrieve patient and care team information for the location from an electronic medical records (EMR) system. The images, the location, and/or the patient and care team information may be communicated to a central video monitoring system.

In some aspects, this disclosure relates to a method for assigning locations to devices. The method comprises: receiving, by a motion sensor in a room of a patient, a signal from a location beacon in the room of the patient corresponding to a location; determining the signal includes a known location identification; and assigning the motion sensor to the location corresponding to the known location identification.

In some aspects, this disclosure relates to a system for assigning locations to devices. The system may comprise one or more 3D motion sensors. The one or more 3D motion sensors may be located to provide the one or more 3D motion sensors with a view of a location of a patient. The 3D motion sensors may be configured to collect a series of images of the location and the patient. The system may comprise a computerized monitoring system. The computerized monitoring system may be communicatively coupled to the one or more 3D motion sensors. The computerized monitoring system may be configured to determine if a location identification is visible on a visual location identifier tag in the location. The computerized communication system may be communicatively coupled to an EMR system. The EMR may be configured to communicate patient and care team information available for the location to the computerized monitoring system.

The location assignment system may further comprise a central video monitoring station. The central video monitoring station may be communicatively coupled to the computerized communication system. The central monitoring station may be configured to display at least a portion of the series of images of the location and the patient and/or information received by the computerized monitoring system. The central video monitoring station may comprise a primary display. The central monitoring station may comprise an alert display. The alert display may be a dedicated portion of the primary display. The alert display may be a separate display or series of displays from the primary display. If the computerized monitoring system detects an unknown device or a device in an unknown location, the computerized communication system may be configured to send an alert to the central monitoring station. The central monitoring station may be configured to move the display of at least a portion of the series of images of the location and the patient from the primary display to the alert display upon receipt of an alert.

In some aspects this disclosure relates to computer-readable storage media having embodied thereon computer-executable instructions. When executed by one or more computer processors the instructions may cause the processors to: receiving from a motion sensor an image of a location corresponding to a patient; determine if a location identification corresponding to the location has been input by a user; upon determining the location identification corresponding to the location has been input by the user, assigning the 3D motion sensor to the location corresponding to the location identification; retrieving, from the EMR system, patient and care team information for the location; and displaying the image of the location and the patient and the patient and care team information for the location.

Additional objects, advantages, and novel features of the disclosure will be set forth in part in the description which follows, and in part will become apparent to those skilled in the art upon examination of the following, or may be learned by practice of the disclosure.

BRIEF DESCRIPTION OF THE SEVERAL VIEWS OF THE DRAWING

The description references the attached drawing figures, wherein:

FIGS. 4-8 are exemplary displays for location assignment systems, in accordance with embodiments of the present disclosure.

DETAILED DESCRIPTION

As noted in the Background, medical facilities, such as hospitals, face many challenges in addition to simply caring for patients. For example, securing patients and equipment (e.g., medical devices) consumes many resources and current methods lack effectiveness. In addition to requiring personnel to physically monitor locations within the facility, visitor logs and visitor badges, and radio-frequency identification (RFID) technology are often utilized to control access to certain locations within the facility. However, each of these require subjective decision-making and are prone to error by the personnel monitoring the locations or assisting visitors signing a visitor log and issuing visitor badges accordingly. Further, none of these methods necessarily prevent an authorized visitor from breaching areas of the facility where the authorized visitor is not authorized. For example, a visitor may be authorized to visit a particular patient but is not authorized to visit another patient or particular areas of the facility. Additionally, in some situations, an authorized visitor may unwittingly provide contraband (e.g., some thing or some object a particular patient is not allowed to possess or be near) to a patient that the current methods are unable to detect. Finally, medical devices are constantly being shuffled between patients and locations within a facility. Tracking the locations of these devices can be extremely difficult. Accordingly, overall security for patients and equipment suffers and the many resources currently being utilized are wasted.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Figure 1:
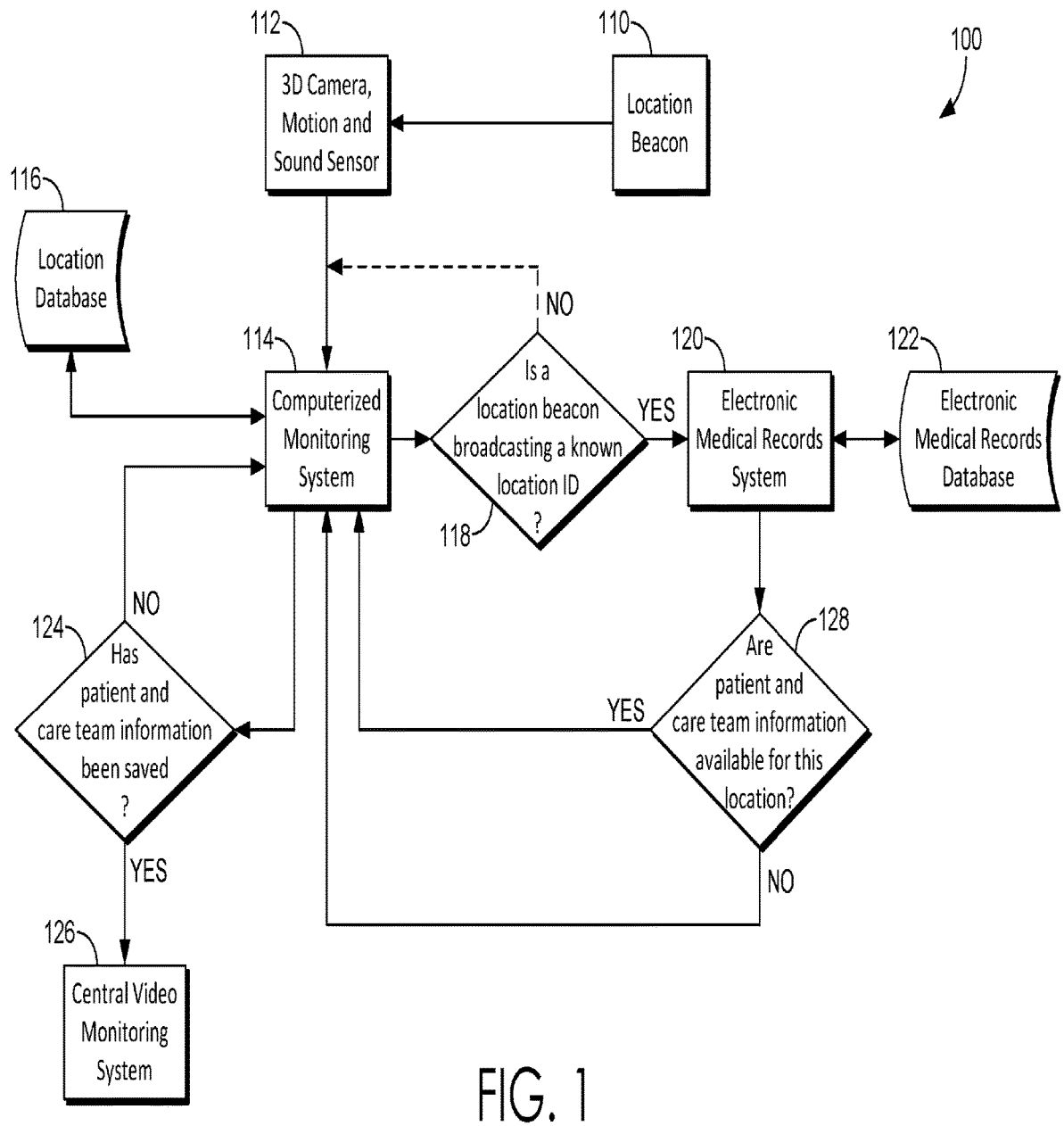
FIGS. 1-3 are exemplary flowcharts for location assignment systems, in accordance with embodiments of the present disclosure.

As shown in FIG. 1, a system for assigning locations to 3D motion sensors 112 having location beacons 110. A 3D motion sensor is an electronic device that contains one or more cameras capable of identifying individual objects, people and motion. The 3D motion sensor may further contain one or more microphones to detect audio. The cameras can utilize technologies including but not limited to color RGB, CMOS sensors, lasers, infrared projectors and RF-modulated light. The 3D motion sensor may have one or more integrated microprocessors and/or image sensors to detect and process information both transmitted from and received by the various cameras. Exemplary 3D motion sensors include the Microsoft® Kinect® Camera, the Sony® PlayStation® Camera, and the Intel® RealSense™ Camera, each of which happens to include microphones, although sound capture is not essential to the practice of the disclosure. A user may be able to configure alerts based on data that is received from the 3D motion sensor 112 and interpreted by the computerized monitoring system 114. For example, a user can configure the computerized monitoring system 114 to provide alerts based on data the computerized monitoring system 114 has interpreted for setting zones in a patient's room, comparing data from multiple systems (RTLS or facial recognition) to determine authorized visitors, a patient crossing a trip wire, falling on the ground, or entering or exiting a safety zone.

As used herein, "a sensor" and "sensors" are used interchangeably in the singular and plural unless expressly described as a singular sensor or an array of sensors. A singular sensor may be used, or a sensor may comprise two or more cameras integrated into a single physical unit. Alternately, two or more physically distinct sensors may be used, or two or more physically distinct arrays of sensors may be used.

A "device" may be any device in the room of a patient being monitored that is movable (e.g., 3D motion sensor) and capable of communicating data to an EMR. As can be appreciated, knowing the location of such a device may be vital to ensuring that the correct information for the correct patient is communicated to the EMR.

As shown in FIG. 1, location assignment system 100 may be utilized to assign the location of a 3D motion sensor 112 in the room of a patient. A 3D motion sensor 112 may be co-located with a patient room to be monitored. The patient room to be monitored may be monitored in a variety of environments, including, without limitation, a hospital, a home, a hospice care facility, a nursing home, an assisted living facility, an outpatient medical care facility, and the like. The 3D motion sensor 112 may be positioned where it is likely to capture images of the patient room to be monitored. For example, a 3D motion sensor 112 may be oriented to take images of a bed, chair, or other location where a patient in the patient room to be monitored may spend a significant amount of time. In some embodiments, the 3D motion sensor 112 may be oriented to take images of persons and/or objects entering and exiting the patient room to be monitored. In some embodiments, the 3D mention sensor 112 may be oriented to take images of equipment (e.g., medical devices) that may be located in the patient room to be monitored. The 3D motion sensor 112 may be permanently installed, or may be temporarily set up in a room as needed. The patient in the patient room to be monitored may be under immediate medical care, e.g., in a medical facility under the supervision of a medical professional, or may not be under immediate care, e.g., in a home or other environment, possibly with a caregiver. A caregiver may be a medical professional or paraprofessional, such as an orderly, nurse's aide, nurse, or the like. A caregiver may also be a friend, relative, individual, company, or facility that provides assistance with daily living activities and/or medical care for individuals, such as individuals who are disabled, ill, injured, elderly, or otherwise in need of temporary or long-term assistance. In some instances, the person to be monitored may be self-sufficient and not under the immediate care of any other person or service provider.

The 3D motion sensor 112 may communicate data, such as images of the patient room being monitored, to a computerized monitoring system 114. The computerized monitoring system 114 is a computer programmed to monitor transmissions of data from the 3D motion sensor 112. The computerized monitoring system 114 may be integral to the 3D motion sensor 112 or a distinctly separate apparatus from the 3D motion sensor 112, possibly in a remote location from 3D motion sensor 112 provided that the computerized monitoring system 114 can receive data from the 3D motion sensor 112. The computerized monitoring system 114 may be located in the monitored patient room, such as a hospital room, bedroom, or living room. The computerized monitoring system 114 may be connected to a central video monitoring system 126. The computerized monitoring system 114 and central monitoring system 126 may be remotely located at any physical locations so long as a data connection exists (USB, TCP/IP or comparable) between the computerized monitoring system 114, the central monitoring system 126, and the 3D motion sensor(s) 112.

The computerized monitoring system 114 may receive data from 3D motion sensor 112 for a monitoring zone (i.e., the patient's room or area to be monitored). Computerized monitoring system 114 may assign reference points to identify the boundaries of the patient identification zone. For example, reference points may be assigned to a perimeter around the patient. It should be understood that the selection of the reference points may vary with the individual and/or the configuration of the location assignment system 100. Reference points may be configured automatically by the location assignment system 100, may be configured automatically by the location assignment system 100 subject to confirmation and/or modification by a system user, or may be configured manually by a system user.

If 3D motion sensor 112 begins to transmit data, computerized monitoring system 114 may, at step 118, assess whether a location beacon 110 on the 3D motion sensor 112 is broadcasting a known location identification. For example, a signal may be received by computerized monitoring system 114 from the location beacon 110 on the 3D motion sensor 112. If no signal is received, the computerized monitoring system 114 may continue to wait for a signal from a location beacon on the 3D motion sensor 112 (or utilize other methods to determine the location identification as described in more detail below with respect to FIGS. 2 and 3) and analyze images in the monitoring zone as long as 3D motion sensor 112 continues to transmit data.

If on the other hand, the location beacon 110 on the 3D motion sensor 112 is broadcasting a known location identification, computerized monitoring system 114 assigns the 3D motion sensor 112 to the location corresponding to the known location identification. The location assignment may be stored in location database 116. Regardless of the signal being received or having a known location identification, images received from the 3D motion sensor 112 may additionally be communicated to central video monitoring system 126.

When the 3D motion sensor 112 has been assigned to the location corresponding to the known location identification, the assignment may be recorded in an EMR 122 by an EMR system 120. If patient and care team information has been saved for the location, at step 124, the location assignment and the patient and care team information are communicated to central video monitoring system 126.

If patient and care team information has not been saved for the location, at step 124, patient and care team information may be retrieved, at step 128, that correspond to the location. This information may be communicated to computerized monitoring system 114 and communicated to central video monitoring system 126 along with the location assignment.

On receiving an image and/or patient and care team information, the central video monitoring system 126, or an attendant there, may receive an alert that provides a live image, video and/or audio feed from the 3D motion sensor 112. One or more caregiver(s) local to patient can be alerted with or even before central video monitoring system 126, so that the caregiver(s) can assess what is happening in person. The priority and timing of alerts to different individuals or stations can be configured in accordance with the needs and desires of a particular facility, experience with a particular monitored individual or type of patient, or any other criterion of the system owner or user. This is true for initial alerts as well as continuing alerts (e.g., if 3D motion sensor 112 is detected in and has not been assigned to a location) or repeated alerts (two or more distinct events where 3D motion sensor 112 is detected and not assigned to a location). The priority and timing of alerts to different individuals may be different for initial, continuing, and/or repeated alerts.

Data associated with alerts may be logged by computerized monitoring system 114 and/or central video monitoring system 126 in a database 116. Data associated with an alert may include, without limitation, the telemetry data from 3D motion sensor 112 that triggered the alert; buffered data preceding the telemetry data that triggered the alert; telemetry data subsequent to the alert; the number and substantive content of an alert; the individual(s) and/or groups to whom an alert was addressed; the response, if any, received or observed following an alert; and combinations thereof.

Figure 2:
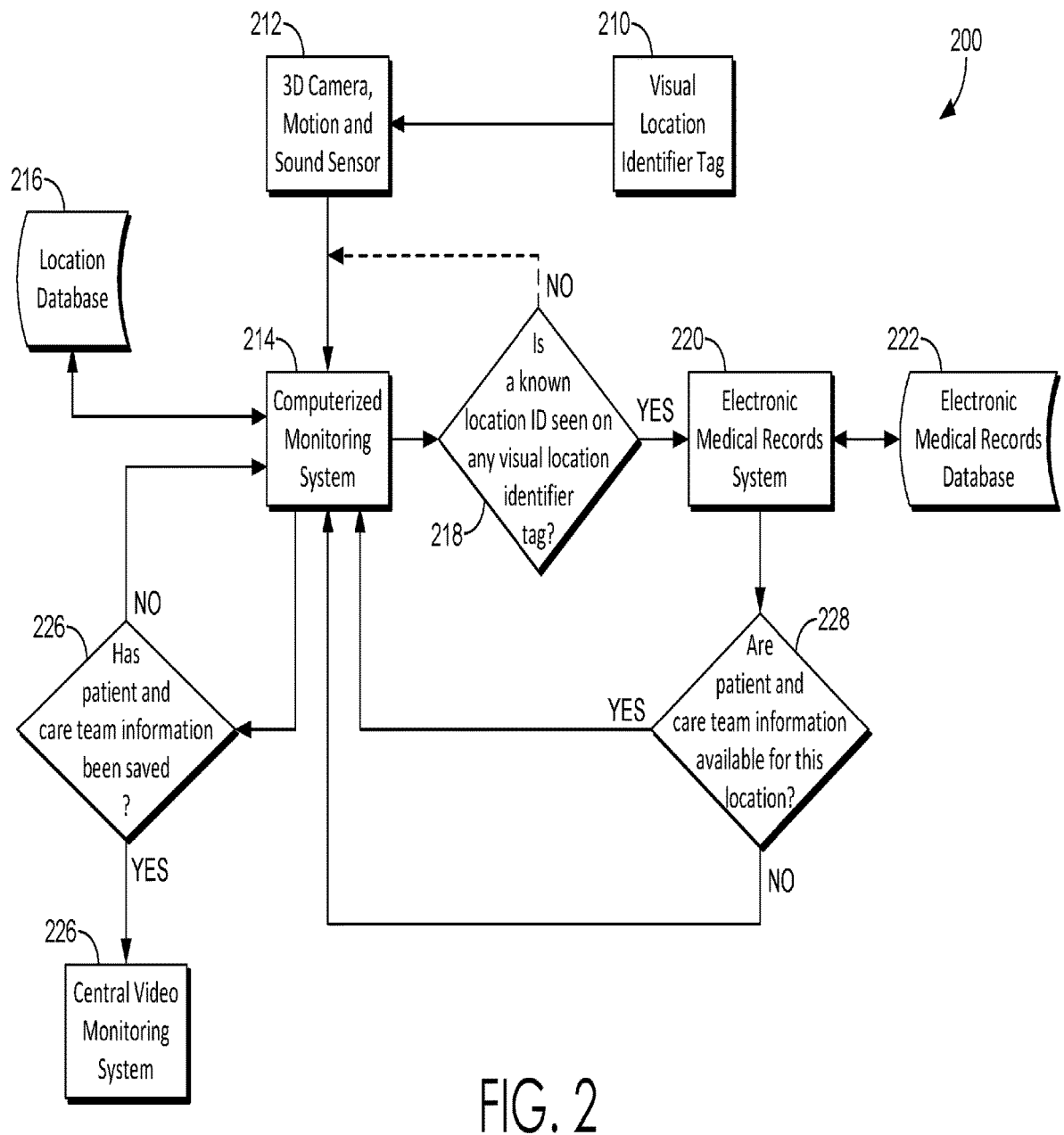

Referring now to FIG. 2, location assignment system 200 may be utilized to assign the location of 3D motion sensor 212 in the room of a patient. A 3D motion sensor 212 may be co-located with a patient room to be monitored. The patient room to be monitored may be monitored in a variety of environments, including, without limitation, a hospital, a home, a hospice care facility, a nursing home, an assisted living facility, an outpatient medical care facility, and the like. The 3D motion sensor 212 may be positioned where it is likely to capture images of the patient room to be monitored. For example, a 3D motion sensor 212 may be oriented to take images of a bed, chair, or other location where a patient in the patient room to be monitored may spend a significant amount of time. In some embodiments, the 3D motion sensor 212 may be oriented to take images of persons and/or objects entering and exiting the patient room to be monitored. In some embodiments, the 3D mention sensor 212 may be oriented to take images of equipment (e.g., medical devices) that may be located in the patient room to be monitored. The 3D motion sensor 212 may be permanently installed, or may be temporarily set up in a room as needed. The patient in the patient room to be monitored may be under immediate medical care, e.g., in a medical facility under the supervision of a medical professional, or may not be under immediate care, e.g., in a home or other environment, possibly with a caregiver. A caregiver may be a medical professional or paraprofessional, such as an orderly, nurse's aide, nurse, or the like. A caregiver may also be a friend, relative, individual, company, or facility that provides assistance with daily living activities and/or medical care for individuals, such as individuals who are disabled, ill, injured, elderly, or otherwise in need of temporary or long-term assistance. In some instances, the person to be monitored may be self-sufficient and not under the immediate care of any other person or service provider.

The 3D motion sensor 212 may communicate data, such as images the patient room being monitored, to a computerized monitoring system 214. The computerized monitoring system 214 is a computer programmed to monitor transmissions of data from the 3D motion sensor 212. The computerized monitoring system 214 may be integral to the 3D motion sensor 212 or a distinctly separate apparatus from the 3D motion sensor 212, possibly in a remote location from 3D motion sensor 212 provided that the computerized monitoring system 214 can receive data from the 3D motion sensor 212. The computerized monitoring system 214 may be located in the monitored patient room, such as a hospital room, bedroom, or living room. The computerized monitoring system 214 may be connected to a central video monitoring system 226. The computerized monitoring system 214 and central video monitoring system 226 may be remotely located at any physical locations so long as a data connection exists (USB, TCP/IP or comparable) between the computerized monitoring system 214, the central monitoring system 126, and the 3D motion sensor(s) 212.

The computerized monitoring system 214 may receive data from 3D motion sensor 212 for a monitoring zone (i.e., the patient's room or area to be monitored). Computerized monitoring system 214 may assign reference points to identify the boundaries of the patient identification zone. For example, reference points may be assigned to a perimeter around the patient. It should be understood that the selection of the reference points may vary with the individual and/or the configuration of the location assignment system 200. Reference points may be configured automatically by the location assignment system 200, may be configured automatically by the location assignment system 200 subject to confirmation and/or modification by a system user, or may be configured manually by a system user.

If 3D motion sensor 212 begins to transmit data in a location, computerized monitoring system 214 may, at step 218, assess whether a known location identification is visible on a visual location identifier tag 210 in the location. For example, computerized monitoring system 214 may receive data from 3D motion sensor 212 that includes a visual location identifier tag. If no such data is received, the computerized monitoring system 214 may continue to wait for a known location identification to be visible on a visual location identifier tag on 210 in the location (or utilize other methods to determine the location identification as described herein with respect to FIGS. 1 and 3) and analyze images in the monitoring zone as long as 3D motion sensor 212 continues to transmit data.

If on the other hand, a known location identification is visible on a visual location identifier tag on 210 in the location, computerized monitoring system 214 assigns the 3D motion sensor 212 to the location corresponding to the known location identification. The location assignment may be stored in location database 216. Regardless of a visual location identifier tag 210 being detected on the 3D motion sensor 212 or having a known location identification, image received from the 3D motion sensor 212 may additionally be communicated to central video monitoring system 226.

When the 3D motion sensor 212 has been assigned to the location corresponding to the known location identification, the assignment may be recorded in an EMR 222 by an EMR system 220. If patient and care team information has been saved for the location, at step 224, the location assignment and the patient and care team information are communicated to central video monitoring system 226.

If patient and care team information has not been saved for the location, at step 224, patient and care team information may be retrieved, at step 228, that correspond to the location. This information may be communicated to computerized monitoring system 214 and communicated to central video monitoring system 226 along with the location assignment.

On receiving the location assignment and/or patient and care team information, the central video monitoring system 226, or an attendant there, may receive an alert that provides a live image, video and/or audio feed from the 3D motion sensor 212. One or more caregiver(s) local to patient can be alerted with or even before central video monitoring system 226, so that the caregiver(s) can assess what is happening in person. The priority and timing of alerts to different individuals or stations can be configured in accordance with the needs and desires of a particular facility, experience with a particular monitored individual or type of patient, or any other criterion of the system owner or user. This is true for initial alerts as well as continuing alerts (e.g., if a 3D motion sensor 212 s detected in and has not been assigned to a location) or repeated alerts (two or more distinct events where a 3D motion sensor 212 is detected and not assigned to a location). The priority and timing of alerts to different individuals may be different for initial, continuing, and/or repeated alerts.

Data associated with alerts may be logged by computerized monitoring system 214 and/or central video monitoring system 226 in a database 216. Data associated with an alert may include, without limitation, the telemetry data from 3D motion sensor 212 that triggered the alert; buffered data preceding the telemetry data that triggered the alert; telemetry data subsequent to the alert; the number and substantive content of an alert; the individual(s) and/or groups to whom an alert was addressed; the response, if any, received or observed following an alert; and combinations thereof.

Figure 3:
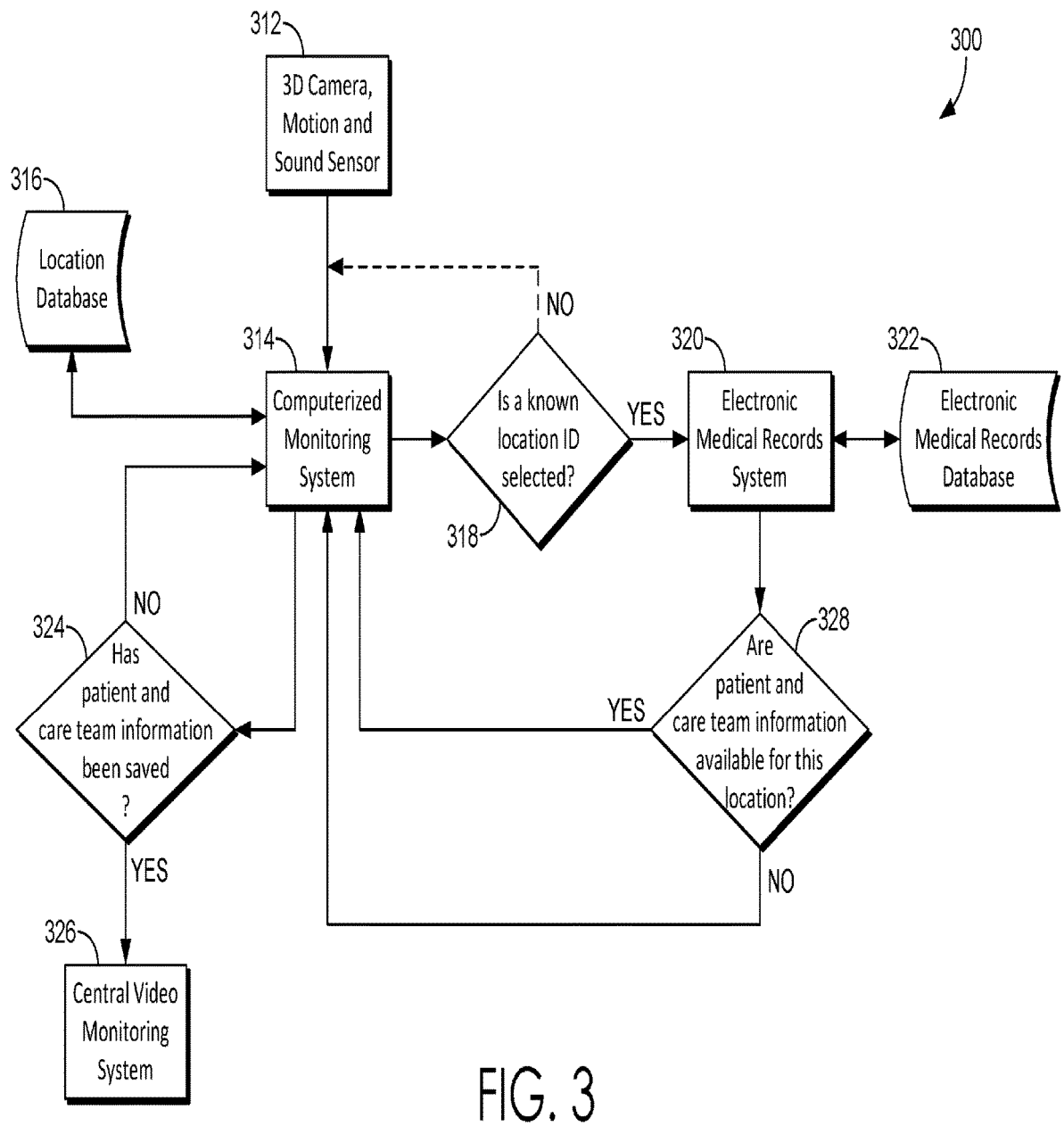

As shown in FIG. 3, location assignment system 300 may be utilized to assign the location of a 3D motion sensor 312 in the room of a patient. A 3D motion sensor 312 may be co-located with a patient room to be monitored. The patient room to be monitored may be monitored in a variety of environments, including, without limitation, a hospital, a home, a hospice care facility, a nursing home, an assisted living facility, an outpatient medical care facility, and the like. The 3D motion sensor 312 may be positioned where it is likely to capture images of the patient room to be monitored. For example, a 3D motion sensor 312 may be oriented to take images of a bed, chair, or other location where a patient in the patient room to be monitored may spend a significant amount of time. In some embodiments, the 3D motion sensor 312 may be oriented to take images of persons and/or objects entering and exiting the patient room to be monitored. In some embodiments, the 3D mention sensor 312 may be oriented to take images of equipment (e.g., medical devices) that may be located in the patient room to be monitored. The 3D motion sensor 312 may be permanently installed, or may be temporarily set up in a room as needed. The patient in the patient room to be monitored may be under immediate medical care, e.g., in a medical facility under the supervision of a medical professional, or may not be under immediate care, e.g., in a home or other environment, possibly with a caregiver. A caregiver may be a medical professional or paraprofessional, such as an orderly, nurse's aide, nurse, or the like. A caregiver may also be a friend, relative, individual, company, or facility that provides assistance with daily living activities and/or medical care for individuals, such as individuals who are disabled, ill, injured, elderly, or otherwise in need of temporary or long-term assistance. In some instances, the person to be monitored may be self-sufficient and not under the immediate care of any other person or service provider.

The 3D motion sensor 312 may communicate data, such as images of the patient room being monitored, to a computerized monitoring system 314. The computerized monitoring system 314 is a computer programmed to monitor transmissions of data from the 3D motion sensor 312. The computerized monitoring system 314 may be integral to the 3D motion sensor 312 or a distinctly separate apparatus from the 3D motion sensor 312, possibly in a remote location from 3D motion sensor 312 provided that the computerized monitoring system 314 can receive data from the 3D motion sensor 312. The computerized monitoring system 314 may be located in the monitored patient room, such as a hospital room, bedroom, or living room. The computerized monitoring system 314 may be connected to a central video monitoring system 326. The computerized monitoring system 314 and central monitoring system 326 may be remotely located at any physical locations so long as a data connection exists (USB, TCP/IP or comparable) between the computerized monitoring system 314, the central monitoring system 326, and the 3D motion sensor(s) 312.

The computerized monitoring system 314 may receive data from 3D motion sensor 312 for a monitoring zone (i.e., the patient's room or area to be monitored). Computerized monitoring system 314 may assign reference points to identify the boundaries of the patient identification zone. For example, reference points may be assigned to a perimeter around the patient. It should be understood that the selection of the reference points may vary with the individual and/or the configuration of the location assignment system 300. Reference points may be configured automatically by the location assignment system 300, may be configured automatically by the location assignment system 300 subject to confirmation and/or modification by a system user, or may be configured manually by a system user.

If a 3D motion sensor 312 begins transmitting, computerized monitoring system 314 may, at step 318, assess whether a location identification has been selected for the 3D motion sensor. For example, the location identification may be selected by a user and received by computerized monitoring system 314 indicating the location of the 3D motion sensor 312. If the location identification has not been selected by a user and received by computerized monitoring system 314, the computerized monitoring system 114 may continue to wait for the location identification of the 3D motion sensor 312 (or utilize other methods to determine the location identification as described in more detail above with respect to FIGS. 1 and 2) and analyze images in the monitoring zone as long as 3D motion sensor 312 continues to transmit data.

If on the other hand, location identification has been selected by a user and is received by computerized monitoring system 314, computerized monitoring system 314 assigns the 3D motion sensor 312 to the location corresponding to the location identification. The location assignment may be stored in location database 316. Regardless of the signal being received or having a known location identification, images received from the 3D motion sensor 312 may additionally be communicated to central video monitoring system 326.

When the 3D motion sensor 312 has been assigned to the location corresponding to the location identification, the assignment may be recorded in an EMR 322 by an EMR system 320. If patient and care team information has been saved for the location, at step 324, the location assignment and the patient and care team information are communicated to central video monitoring system 326.

If patient and care team information has not been saved for the location, at step 324, patient and care team information may be retrieved, at step 328, that correspond to the location. This information may be communicated to computerized monitoring system 314 and communicated to central video monitoring system 326 along with the location assignment.

On receiving the location assignment and/or patient and care team information, the central video monitoring system 326, or an attendant there, may receive an alert that provides a live image, video and/or audio feed from the 3D motion sensor 312. One or more caregiver(s) local to patient can be alerted with or even before central video monitoring system 326, so that the caregiver(s) can assess what is happening in person. The priority and timing of alerts to different individuals or stations can be configured in accordance with the needs and desires of a particular facility, experience with a particular monitored individual or type of patient, or any other criterion of the system owner or user. This is true for initial alerts as well as continuing alerts (e.g., if a 3D motion sensor 312 is detected in and has not been assigned to a location) or repeated alerts (two or more distinct events where a 3D motion sensor 312 is detected and not assigned to a location). The priority and timing of alerts to different individuals may be different for initial, continuing, and/or repeated alerts.

Data associated with alerts may be logged by computerized monitoring system 314 and/or central video monitoring system 326 in a database 316. Data associated with an alert may include, without limitation, the telemetry data from 3D motion sensor 312 that triggered the alert; buffered data preceding the telemetry data that triggered the alert; telemetry data subsequent to the alert; the number and substantive content of an alert; the individual(s) and/or groups to whom an alert was addressed; the response, if any, received or observed following an alert; and combinations thereof.

Figures 4, 5:
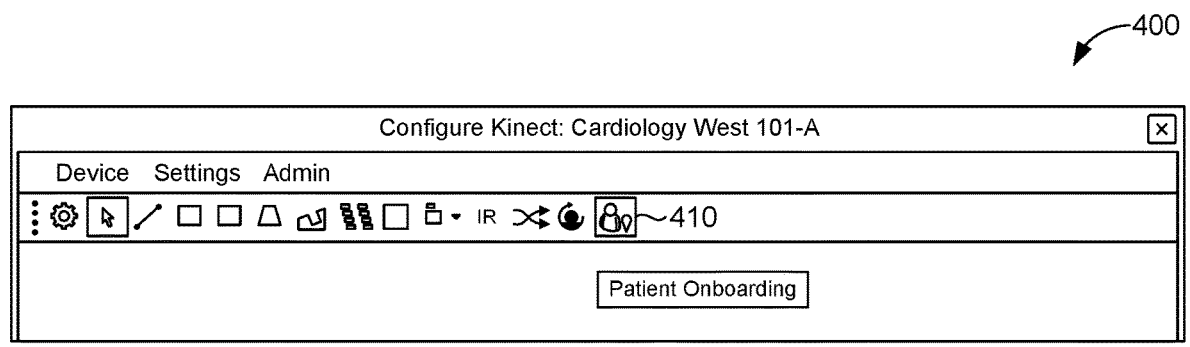
Figure 6:
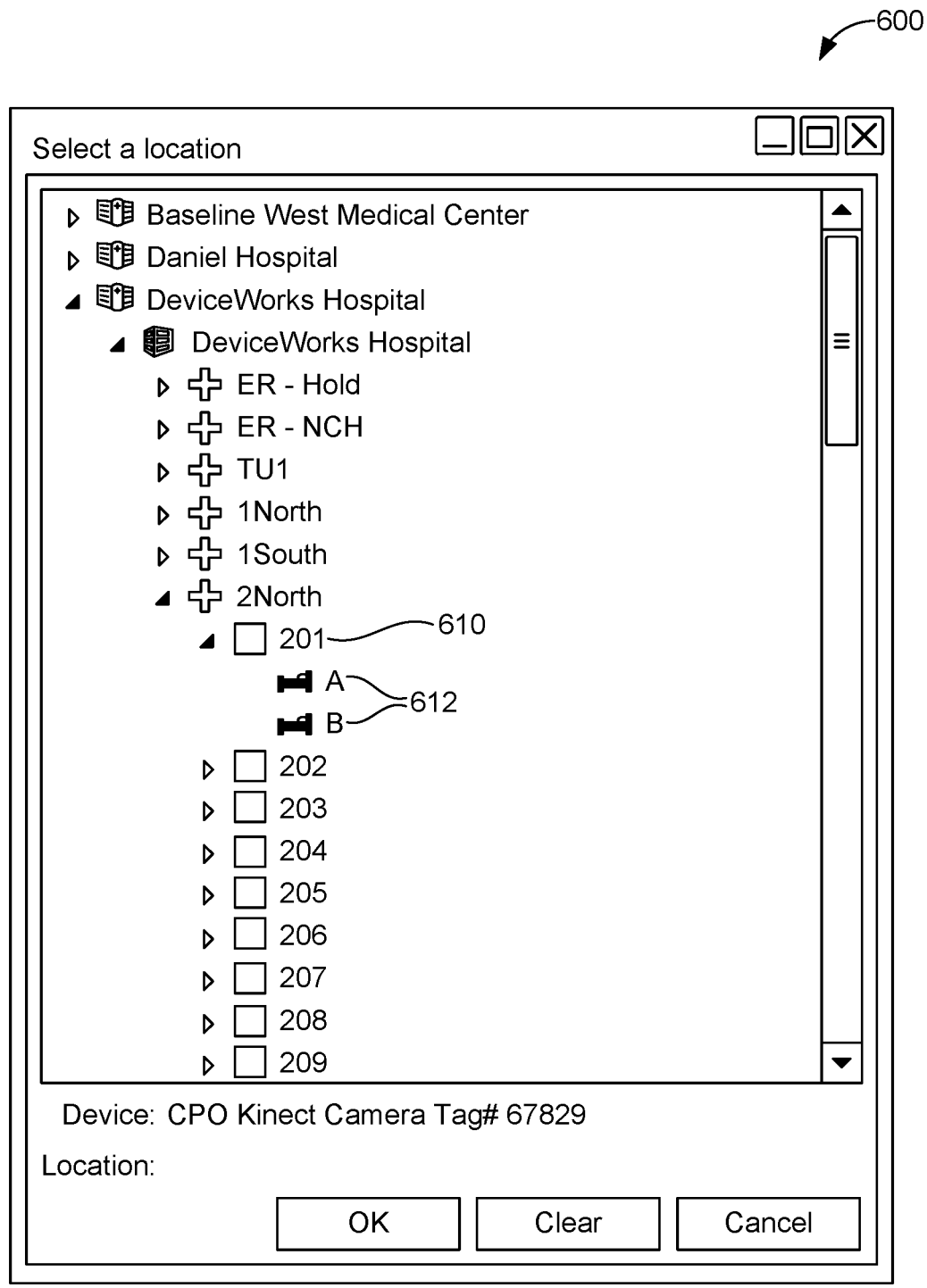

FIG. 4 shows an exemplary view for location assignment 400. As illustrated, a clinician may select a patient onboarding icon 410 to begin the process of assigning a 3D motion sensor to a location. In FIG. 5, a patient onboarding view 500 illustrates a bed icon 510 that can be selected to assign a device to a location manually or employ one of the automatic location assignment options (such as the options discussed with reference to FIGS. 1 and 2). FIG. 6 illustrates a location view that enables a clinician to select a room 610 and/or bed 612 to assign the 3D motion sensor to the corresponding location (i.e., the room and/or bed). Once selected, patient and care team demographics 710 may be populated based on the selection 720, as illustrated in the populated onboarding view 700 in FIG. 7. Accordingly, as shown in FIG. 8, the patient demographics and care team information, as well as any images (such as those corresponding to the patient, the patient room, and/or the location assignment) are provided in video feed 800.

The various computerized systems and processors as described herein may include, individually or collectively, and without limitation, a processing unit, internal system memory, and a suitable system bus for coupling various system components, including database 118, with a control server. Computerized patient monitoring system 106 and/or central video monitoring system 116 may provide control server structure and/or function. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus.

The computerized systems typically include therein, or have access to, a variety of computer-readable media, for instance, database 116. Computer-readable media can be any available media that may be accessed by the computerized system, and includes volatile and nonvolatile media, as well as removable and non-removable media. By way of example, and not limitation, computer-readable media may include computer-storage media and communication media. Computer-readable storage media may include, without limitation, volatile and nonvolatile media, as well as removable and non-removable media implemented in any method or technology for storage of information, such as computer readable instructions, data structures, program modules, or other data. In this regard, computer-storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server. Computer-readable storage media excludes signals per se.

Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media. The computer-readable storage media discussed above, including database 116, provide storage of computer readable instructions, data structures, program modules, and other data for the computerized systems. Computer readable instructions embodied on computer-readable storage media may be accessible by location assignment system 100 and/or component(s) thereof, and, when executed by a computer processor and/or server, may cause the system to function and/or perform the methods described herein.

The computerized systems may operate in a computer network using logical connections to one or more remote computers. Remote computers may be located at a variety of locations, for example, but not limited to, hospitals and other inpatient settings, veterinary environments, ambulatory settings, medical billing and financial offices, hospital administration settings, home health care environments, payer offices (e.g., insurance companies), home health care agencies, clinicians' offices and the clinician's home or the patient's own home or over the Internet. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers may also be physically located in non-traditional medical care environments so that the entire health care community may be capable of integration on the network.

The remote computers may be personal computers, servers, routers, network PCs, peer devices, other common network nodes, or the like, and may include some or all of the elements described above in relation to the control server. The devices can be personal digital assistants or other like devices.

Exemplary computer networks may include, without limitation, local area networks (LANs) and/or wide area networks (WANs). Such networking environments are commonplace in offices, enterprise-wide computer networks, intranets, and the Internet. When utilized in a WAN networking environment, the control server may include a modem or other means for establishing communications over the WAN, such as the Internet. In a networked environment, program modules or portions thereof may be stored in the control server, in the database 118, or on any of the remote computers. For example, and not by way of limitation, various application programs may reside on the memory associated with any one or more of the remote computers. It will be appreciated by those of ordinary skill in the art that the network connections shown are exemplary and other means of establishing a communications link between the computers may be utilized.

In operation, a user may enter commands and information into the computerized system(s) using input devices, such as a keyboard, a pointing device (commonly referred to as a mouse), a trackball, a touch pad, a 3D Gesture recognition camera or motion sensor. Other input devices may include, without limitation, microphones, satellite dishes, scanners, or the like. In addition to or in lieu of a monitor, the computerized systems may include other peripheral output devices, such as speakers and a printer.

Many other internal components of the computerized system hardware are not shown because such components and their interconnection are well known. Accordingly, additional details concerning the internal construction of the computers that make up the computerized systems are not further disclosed herein.

Methods and systems of embodiments of the present disclosure may be implemented in a WINDOWS or LINUX operating system, operating in conjunction with an Internet-based delivery system, however, one of ordinary skill in the art will recognize that the described methods and systems can be implemented in any operating system suitable for supporting the disclosed processing and communications. As contemplated by the language above, the methods and systems of embodiments of the present invention may also be implemented on a stand-alone desktop, personal computer, cellular phone, smart phone, tablet computer, PDA, or any other computing device used in a healthcare environment or any of a number of other locations.

From the foregoing, it will be seen that this disclosure is well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

What is claimed is:

1. A computerized method for assigning locations to 3D motion sensors, the computerized method comprising:

receiving, from a motion sensor, a signal including one or more images;
determining that a motion sensor's location is unassigned in a location database;
responsive to determining that the motion sensor's location is unassigned, determining that a location identification tag is visible within at least one of the one or more images received from the motion sensor; and
automatically assigning the motion sensor to a location corresponding to the location identification tag in the location database.

2. The computerized method of claim 1, wherein the location database is within an EMR system and the computerized method further comprises retrieving, from the EMR system, patient information and care team information for the location.

3. The computerized method of claim 2, further comprising communicating the patient information and the care team information for the location to a central video monitoring system.

4. The computerized method of claim 3, wherein the central video monitoring system comprises a primary display and an alert display.

5. The computerized method of claim 4, wherein the alert display is a dedicated portion of the primary display.

6. The computerized method of claim 4, wherein the alert display is a display or series of displays separate from the primary display.

7. The computerized method of claim 1 further comprising sending an alert to a clinician present at the location with one or more of a live image, video and/or audio feed from the motion sensor assigned to the location.

8. The computerized method of claim 7 further comprising sending an alert to a central video monitoring system, wherein the alert to the clinician present at the location is sent prior to the alert sent to the central video monitoring system.

9. The computerized method of claim 7 further storing a response taken in response to the alert to the clinician present at the location.

10. The computerized method of claim 7 further comprising storing content of the alert to the clinician present at the location.

11. A computing system comprising:
a motion sensor configured to collect images;
a computerized monitoring system communicatively coupled to the motion sensor, the computerized monitoring system configured to:
receive, from the motion sensor, one or more images;
determine if a location identification for the motion sensor has been input by a user;
upon determining no location identification has been input by the user for the motion sensor, determine that a location identification is visible on a location identifier tag in at least one of the one or more images from the motion sensor;
based on determining the location identification is visible in the at least one of the one or more images from the motion sensor, automatically assign the motion sensor to a location corresponding to the location identification; and
send an assignment of the motion sensor to the location for recording in a location database.

12. The computing system of claim 11, where the location corresponds to an individual.

13. The computing system of claim 11, wherein the computerized monitoring system is further configured to retrieve patient information and care team information for the location.

14. The computing system of claim 13, wherein the computerized monitoring system is further configured to display the one or more images and the patient information and the care team information for the location.

15. The computing system of claim 11, wherein the location database is within an EMR system.

16. The computing system of claim 11 further comprising a central video monitoring system coupled to the computerized monitoring system, the central video monitoring system configured to display at least a portion of the one or more images from the motion sensor.

17. The computing system of claim 16, wherein the computerized monitoring system is further configured to send an alert to a clinician present at the location with one or more of a live image, video and/or audio feed from the motion sensor assigned to the location.

18. The computing system of claim 17, wherein the computerized monitoring system is configured to send the alert to the clinician present at the location prior to an alert being sent to the central video monitoring system.

19. The computing system of claim 11, wherein the location identification that is visible within the one or more images comprises a bar code, QR code, or a distinct object or symbol corresponding to the location.

20. The computing system of claim 11, wherein the motion sensor is positioned within a patient room to capture images of a patient.

* * * * *